United States Patent [19]

Kuperus

[11] Patent Number: 4,638,809
[45] Date of Patent: Jan. 27, 1987

[54] METHOD OF PREPARING RADIONUCLIDE DOSES

[76] Inventor: John H. Kuperus, 10430 Mohawk, Cypress, Calif. 90630

[21] Appl. No.: 592,091

[22] Filed: Mar. 22, 1984

[51] Int. Cl.⁴ .................................................. A61B 5/14
[52] U.S. Cl. ..................... 128/653; 128/763; 128/1.1; 604/87
[58] Field of Search ............... 128/653, 654, 655, 1.1, 128/1.2, 760, 763–765; 604/38, 82, 85–92, 121, 190, 191, 199, 200, 201, 206, 232, 254, 240–241, 266; 250/303, 506.1, 496.1, 492.1; 206/219, 221, 568–571

[56] References Cited

U.S. PATENT DOCUMENTS

| | | | |
|---|---|---|---|
| 3,756,390 | 9/1973 | Abbey et al. | 604/87 |
| 3,801,818 | 4/1974 | Hulit et al. | 250/496.1 |
| 3,814,941 | 6/1974 | Czaplinski | 128/1.1 |
| 4,361,155 | 11/1982 | Anastasio | 128/763 |
| 4,479,578 | 10/1984 | Brignola et al. | 206/221 |

Primary Examiner—Edward M. Coven
Attorney, Agent, or Firm—Charles H. Thomas

[57] ABSTRACT

Dosages of a radionuclide carrier for use in diagnostic nuclear medicine are prepared in separate, aliquot quantities by storing a discrete amount of a lyophilized radionuclide carrier material in tubular containers. The containers are closed to exclude moisture and air. The radionuclide carrier is reconstituted as an aliquot dosage by interposing the container between the needle and barrel of a hypodermic syringe, and drawing a predetermined amount of a reconstituting liquid into the syringe barrel through the needle and through the container. The liquid dissolves the lyophilized carrier to form an aliquot dosage for each patient, only as needed.

7 Claims, 4 Drawing Figures

METHOD OF PREPARING RADIONUCLIDE DOSES

BACKGROUND OF THE INVENTION

1. Field of the Invention

The present invention relates to the preparation of dosages of tracer materials for use in diagnostic nuclear medicine.

2. Description of the Prior Art

Nuclear medicine has become an extremely valuable tool for diagnosing medical ailments. Abnormalities in the soft tissue of the organs of the body can be detected in a non-invasive fashion. Diagnostic nuclear medicine typically involves the detection of a tracer quantity of an injected substance containing a known, low-level dosage of a radionuclide.

The chemical composition of the radionuclide is such that it is compatible with carrier materials and with the body chemistry of patients. The molecules containing the radionuclides are attached to molecules of a carrier material which is chosen to exhibit an affinity for migration toward particular areas of the human body. For example, radionuclide carriers are commercially available which, when injected into a patient, will tend to migrate toward the patient's bones, heart, brain, kidneys, gall bladder, lungs, and liver. Migration of the carrier toward the selected region of the body occurs through the circulatory system of the patient.

Circulatory abnormalities in particular portions of the body are detected by comparing the circulation of the carrier and radionuclide in a particular patient with the corresponding circulation in patients known to be normal and in patients known to be abnormal in certain regards.

As the carrier and radioactive dosage are carried through a patient's circulatory system, some of the radionuclides will decay, thus emitting detectable rays, such as gamma rays. Gamma rays pass through the body of a patient and can be detected by such devices as scintillation detectors. Scintillation detectors are typically formed with sodium iodide crystals which emit flashes of light when subjected to gamma radiation. The locations of the flashes of light of the decaying radionuclides are ascertained through one or more devices such as photomultiplier tubes. Photomultiplier tubes convert visible flashes of light into electrical pulses.

While several different radionuclides exist which can be employed in nuclear medicine, the most widely used substance is technetium - 99m. Technetium - 99m is the tracing material of choice in the vast majority of diagnostic tests in the field of nuclear medicine. Technetium - 99m has a half life of only six hours so that the level of radioactivity in a tracer dose administered to a patient decays rapidly. Also, because the half life of technetium - 99m is so short a relatively low dosage of the substance will produce a significant number of nuclear events which can be detected to analyze any abnormality in the patient. Also, the rapid decay of the tracer quantity of material poses a minimum health hazard to the patient and allows a fairly rapid sequence of tests utilizing radioactive substances to be performed without interference from remnant traces of prior dosages from earlier tests.

Technetium - 99m will attach readily to a number of different carrier compounds which will selectively migrate toward locations of interest in the body of the patient to which the carrier is administered. For example, stannous pyrophosphate will migrate toward the heart and the bones of a patient. Stannous methylene diphosphonate, when injected, will tend to collect in the bones of a patient. Stannous glucoheptonate migrates toward the brain and kidneys of a patient. Stannous HIDA shows an affinity for a patient's gall bladder. Stannous macroaggregated albumin tends to collect in the lungs of a patient. Stannous microaggregated albumin migrates toward the patient's liver. Stannous DTPA tends to migrate towards a patient's brain and kidneys. Stannous dimercaptosuccinic acid shows an affinity toward a patient's kidneys.

All of the foregoing materials which exhibit a particular affinity for the organs or regions of the body indicated are normally stored in lyophilized form. That is, the substances are freeze-dried and can be reconstituted with liquids. When mixed with a saline solution containing sodium technetium pertechnetate the foregoing tracer compounds will dissolve almost instantly and combine with the technetium pertechnetate. The mixture can then be used as a tracer material useful in diagnostic tests in the field of nuclear medicine.

According to conventional practice, patients are scheduled for particular diagnostic tests which employ radionuclides and carrier materials, such as those specified, which show an affinity towards specific portions of the body of a living subject. According to conventional practice, a batch of a tracing substance is prepared each morning in the nuclear medicine laboratory of a hospital for each different test scheduled to be administered during the course of the day. The technetium pertechnetate substance is produced and stored in a lead-lined container known as a "pig". The "pigs" are labeled according to the stannous compound which is to be introduced therein. A saline solution of sodium technetium pertechnetate having a radioactivity level of typically between 200 and 300 millicuries is introduced into each "pig". A quantity of a lyophilized stannous compound for each test to be performed during the course of the day is mixed into the saline pertechnetate solution in each "pig". Separate dosages are withdrawn from the appropriate "pigs" as required, and are injected into the patient.

Several problems exist in connection with the present method of preparing doses of a tracing substance for use in nuclear medicine. Specifically, as the radionuclide compound sits in the "pig" throughout the course of the day, it tends to separate from the carrier chemical. Accordingly, the level of radioactive material carried to the organ or portion of the body of interest by a dosage drawn late in the day is likely to be less than the corresponding level for a test performed early in the morning. Also, as the liquid mixtures are prepared in each "pig" for the different diagnostic tests involved, relatively large quantities of the technetium tracer are committed for use with particular carrier materials. That is, for example, if a number of bone scans are scheduled for a particular day, the technician in the nuclear medicine laboratory will mix a quantity of stannous pyrophosphate with an amount of technetium pertechnetate more than sufficient to perform the number of bone scans scheduled for that day. However, if one of the bone scans is cancelled and an unscheduled lung scan is to be performed, an entirely new batch of tracing substance must be prepared. Consequently, the technician is exposed to an inordinately great level of radiation since each batch of tracing substance which is mixed will have a level of radioactivity of between about 200 and 300 millicuries. The technician is therefore exposed to the level of radiation necessary to prepare batches of tracing material for all of the tests which are to be performed during the day.

A further problem which arises in the conventional method of preparing doses of a tracing substance is that dosages of a radioactive tracing substance will sometimes be drawn from the wrong "pig". Errors of this type frequently occur due to labeling errors on the "pig", different lyophilized carriers are introduced into the "pigs" on different days. When a scan is performed of a patient to whom a dosage with an incorrect carrier has been administered, the test results are meaningless and the test must be repeated.

A further problem with the conventional practice is that much of the radionuclide dosage prepared is wasted. For example, a saline solution of sodium technetium pertechnetate having an initial radioactivity level of 300 millicuries is normally introduced into each "pig" in the morning. However, during the course of the day, perhaps only one or two doses of the tracing substance may be drawn from each different "pig". Since each dose to be injected into a patient has a radioactivity level of about 25 millicuries, technicians in nuclear medicine laboratories are subjected to inordinately large levels of radioactivity. Furthermore, once the level of radioactivity has decayed to where the dosages are no longer usable, disposal of the unused radioactive material becomes a problem.

SUMMARY OF THE INVENTION

The present invention is a method of preparing aliquot doses of a tracer material useful in diagnostic nuclear medicine. The method involves storing discrete quantities of a lyophilized radionuclide carrier in separate tubular containers from which moisture and oxygen are excluded by packing the containers in a nitrogen atmosphere. As a particular carrier is to be used, a predetermined amount of a liquid containing a radionuclide in known concentration is drawn into the hypodermic syringe barrel through the hypodermic needle. One of the containers is interposed between the syringe barrel and needle either before or after the reconstituting liquid is drawn. The liquid is passed through the container, either while the liquid is being drawn or as it is being ejected from the barrel. In both cases the discrete quantity of lyophilized radionuclide carrier is quickly dissolved when it meets the liquid, and, with the liquid containing the radionuclide, forms an aliquot dosage of the tracer material. Moeover, each dosage is formed only as it is required.

According to the present invention all of the radioactive substance to be used in all of the tests is stored in a single "pig". It is, therefore, impossible for material to be withdrawn from the wrong "pig", since but a single source of liquid containing the radioactive material is employed. As a result, there is far less likelihood of preparing a dose of the wrong radioactive tracing substance, according to the present invention.

It is not necessary for the reconstituting liquid to be radioactive. For example, a non-radioactive liquid can be passed through the tubular container in which an aliquot quantity of stannous pyrophosphate is stored. The contents of the syringe can be injected into the patient. The pyrophosphate anions attach themselves to the red blood cells of the patient. Some time elapses before the attachment process proceeds to a significant degree. When doses of a radioactive tracing substance are administered according to conventional practice, the level of radioactivity declines to a significant extent before a scan can be performed. However, with the method of the present invention, the technetium pertechnetate need not be included in the reconstituting liquid which is initially injected into the patient. Accordingly, the saline solution of technetium pertechnetate is injected into the patient about 20 minutes to a half an hour after the injection of the stannous pyrophosphate. The level of the radioactivity dose administered to the patient is no greater than with the use of conventional procedures, yet the amount of radioactivity which can be detected is greater. The reliability of the results of the test is therefore improved.

The invention may be described with greater clarity and particularity by reference to the accompanying drawings.

DESCRIPTION OF THE IMPLEMENTATION

Figure 1:
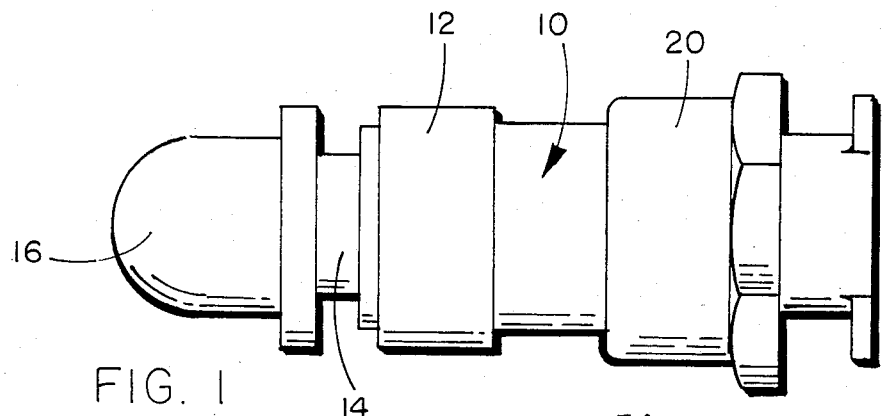
FIG. 1 is a perspective elevational view of a tubular container used in the method of the invention, sealed at both ends.
Figure 3:
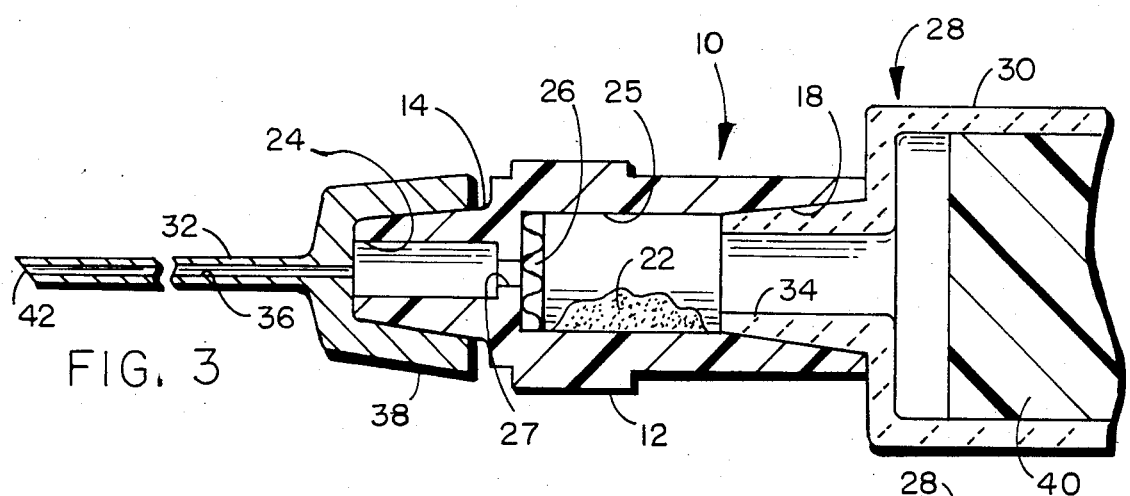
FIG. 3 is a sectional elevational view illustrating the interposition of the container of FIG. 1 between the hypodermic needle and barrel of FIG. 2 prior to drawing a reconstituting liquid into the barrel.

FIG. 1 illustrates a tubular, generally cylindrical annular container 10. The container 10 is a plastic structure molded with a raised, integrally formed collar 12 near one end. The container 10 is open at both ends. At one end a nose 14 is defined with a convex, frusto-conical outer surface, as depicted in FIG. 3. The central passageway 24 defined in the nose 14 is closed by a dome-shaped plastic or rubber cap 16, as depicted in FIG. 1. The opposite end of the container 10 is formed with an internal frusto-conical surface 18, best depicted in FIG. 3, which is closed by a rubber or plastic cap 20 as depicted in FIG. 1.

FIG. 3 illustrates the placement of a quantity 22 of a lyophilized radionuclide carrier for storage into the tubular container 10. The internal, frusto-conical surface 18 forms an opening at one end of the container 10, while the passageway 24 is defined within the nose 14 of the opposite end of the container 10. The container 10 is formed with a cylindrical cavity 25 between the passageway 24 and the opening defined by the surface 18.

Preferably, a disc-shaped filter 26 is positioned in the cylindrical cavity 25 in the container 10 at the inlet 27 thereto from the passageway 24. The filter 26 is preferably constructed in a manner comparable to a filter as employed in a conventional intervenous (IV) duct. That is, the filter 26 has openings of between about 5 and about 50 microns. While the quantity 22 of carrier material is illustrated as being located within the cylindrical cavity defined in the container 10, the carrier material may also be located within the filter 26. If the material is within the filter 26, it will be trapped therewithin until a reconstituting liquid is drawn through the container 10. However, once a reconstituting liquid enters the filter 26, the carrier material will be readily dissolved and carried therefrom.

Quantities of lyophilized carrier material may be stored within a number of different containers 10 for prolonged periods of time. The caps 16 and 20 exclude air and moisture from the cavities defined within the containers 10.

To prepare aliquot doses of a tracer material, a container 10 must be employed in association with a hypodermic syringe 28 having a cylindrical barrel 30 and a hypodermic needle 32. The hypodermic needle 32 is normally mounted on a nipple 34 protruding axially from the barrel 30. The nipple 34 is formed with a convex, frusto-conical surface, and the configuration of the nose 14 of the container 10 is constructed in the same size and shape as the corresponding surface of the nipple 34. The hypodermic needle 32 is formed with a central, axial duct 36. The needle 32 includes a piercing end 42 for pentrating the skin of a patient as painlessly as possible, and defines an enlarged, cup-shaped fitting 38 at its opposite end. The fitting 38 has a concave frusto-conical surface which seats snugly by friction on the nipple 34 to form an airtight and liquid tight seal therewith.

To prepare aliquot doses of a tracer material useful in diagnostic nuclear medicine studies according to the invention, it is necessary to first store a discrete quantity of a lyophilized radionuclide carrier in the tubular container 10. The carrier material is depicted at 22 in FIG. 3, and is typically in the form of a powder. The carrier chosen for storage has an affinity for specific portions of the body of a living subject once it is dissolved and injected into the subject. The carrier is transported through the circulatory system of the subject. A quantity of 2 milligrams of carrier material is a recommended dosage for most patients. This quantity will provide more than enough binding sites for the technetium protechnetate - 99m.

Numerous containers 10 are employed for storing discrete, unit dosages for the different carrier materials which are likely to be required for nuclear medicine studies in a hospital. Exemplary carriers have heretofore been identified, and the containers for each different type of carrier must be clearly marked with the identity of the carrier. Marking can be achieved with color coding as well as appropriate labeling.

Once the unit dosage of a carrier material has been placed in a container 10, the open ends of the container 10 are closed with the caps 16 and 20. The lyophilized carrier material can then be preserved indefinitely in an aliquot dosage form. The end caps 16 and 20 seal the container 10 so that moisture is excluded from the cavity 25 therewithin.

Figure 2:
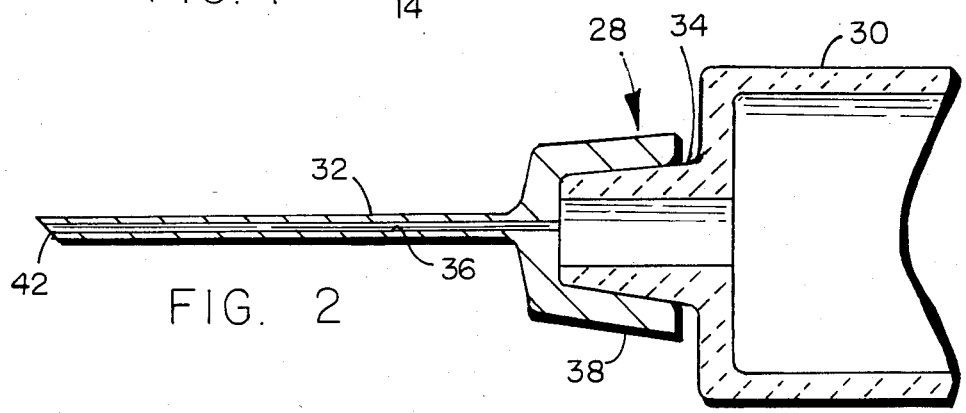
FIG. 2 is a sectional elevational view illustrating the customary position of a hypodermic needle on the barrel of a hypodermic syringe.

When a particular nuclear medicine study is required, a container 10 holding an aliquot dose of the appropriate carrier material is taken from storage. A hypodermic syringe 28, depicted in FIG. 2, is necessary to administer the dosage. The needle 32 of the hypodermic syringe 28 is normally mounted on the nipple 34 of the barrel 30 in the manner depicted in FIG. 2. To practice the invention, however, the selected container 10 must first be positioned between the barrel 30 and the needle 32 of the hypodermic syringe 28. This is easily achieved simply by pulling the needle 32 from the nipple 34. The end caps 16 and 20 are removed from the selected container 10 and the container 10 is placed on the nipple 34 with the concave frusto-conical surface 18 residing in contact with the nipple 34 and with the convex frusto-conical surface of the container nose 14 in frictional engagement with the cup-shaped fitting 38 of the needle 32, as depicted in FIG. 3. The contacting surfaces of the container 10 and the parts of the hypodermic syringe 28 are quite smooth, and mere frictional engagement with the facing surfaces is sufficient to form fluid tight seals.

Figure 4:
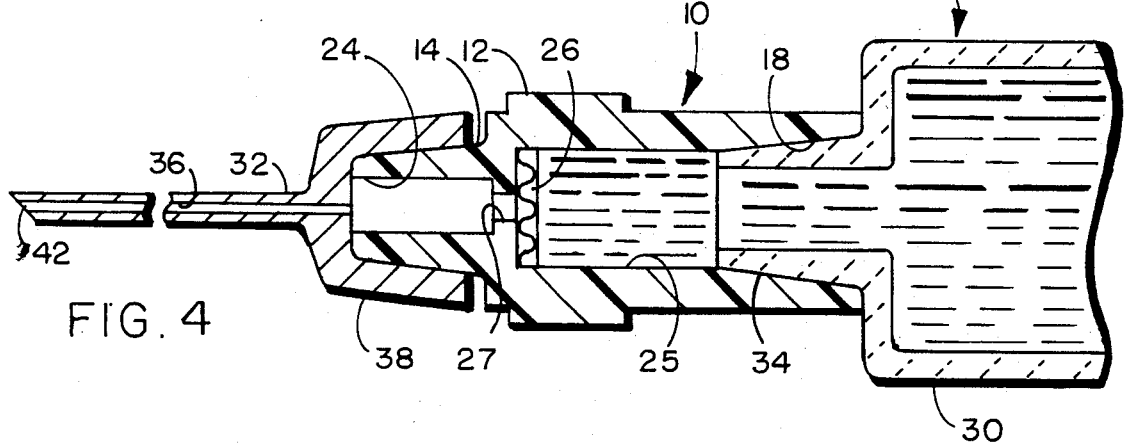
FIG. 4 illustrates the hypodermic needle, the carrier container, and the hypodermic barrel of FIG. 3 after the reconstituting liquid has been drawn.

The plunger 40 of the syringe 28 is advanced to its limit toward the nipple 34. The tip 42 of the needle 32 is then placed into a reservoir containing a reconstituting liquid. In most nuclear medicine tests the reconstituting liquid will be a saline solution of sodium technetium pertechnetate - 99m. The plunger 40 within the syringe 28 is then drawn away from the nipple 34 so that the reconstituting liquid is drawn into the hypodermic barrel 30 through the hypodermic needle 32 and through the container 10. Almost immediately upon contact with the reconstituting liquid, the quantity 22 of the lyophilized carrier material is dissolved. About one-half of a cubic centimeter of reconstituting liquid is drawn into the barrel 30. The technetium protechnetate in such a dose will typically have a radioactivity level of approximately 25 millicuries. The mixture of the lyophilized carrier and the reconstituting liquid, depicted at 44 in FIG. 4, forms an administerable dose of a tracing substance for use in nuclear medicine. The dose may be injected directly into the circulatory system of the patient using the hypodermic syringe 28. As the tracing substance is injected, the filter 26 prevents any undissolved carrier material from entering the circulatory system of the patient. Once the dosage of the tracing substance has been injected, the nuclear medicine study may commence.

Undoubtedly, numerous variations and modifications of the invention will become readily apparent to those familiar with techniques for preparing injections for use in nuclear medicine. Accordingly, the scope of the invention should not be construed as limited to the specific implementation of the method described herein, but rather is defined in the Claims appended hereto.

I claim:

1. A method of preparing aliquot dosea of a tracer material useful in diagnostic nuclear medicine comprising:
   storing descrete quantities of a lyophilized radionuclide carrier in separate tubular containers from which air and moisture is excluded,
   selecting from said tubular containers a container in which is stored a carrier appropriate for a nuclear diagnostic test to be performed,
   interposing said selected container between the needle and the barrel of a hypodermic syringe, and drawing a predetermined amount of a liquid containing a radionuclide tracer in known concentration into said hypodermic syringe barrel through said hypodermic needle and through said selected container to disolve the discrete quantity of lyophilized carrier therein to combine said carrier with said redionuclide tracer to form an aliquot dose of nuclear diagnostic tracer material, as needed.

2. A method according to claim 1 further comprising passing said liquid through a filter as it is drawn into said container.

3. A method according to claim 1 further comprising passing said liquid through a filter having a pore size of about 5 microns, as said liquid is drawn into said container.

4. A method of preparing doses of a radioactive tracing substance for use in nuclear diagnostic medicine comprising:

placing a quantity of a lyophilized radionuclide carrier into a tubular container having openings at both ends while said tubular container is in an inert atmosphere, closing both of said ends of said tubular container to exclude air and moisture therefrom so as to preserve said quantity of said lyophilized carrier as an aliquot dose, storing said quantity of lyophilized carrier in said container, opening both ends of said container, interposing said container between a needle and a barrel of a hypodermic syringe with one end of said container in communication with said needle and the other end of said container in communication with said barrel, mixing said lyophilized carrier with a liquid containing a predetermined amount of a radionuclide tracer by drawing said liquid into said barrel through said syringe needle and said container, and ejecting said liquid from said barrel through said tubular container and through said needle.

5. A method according to claim 4 further comprising filtering said liquid as it passes through said needle and through said container.

6. A method according to claim 4 further comprising passing said liquid through a filter of between about 5 and about 50 microns as said liquid is ejected through said barrel, said container, and said needle.

7. A method of preparing dose of a tracing substance for use in nuclear medicine comprising:

introducing a lyophilized material having an affinity for specific portions of the body of a living subject, into a container having access apertures at its opposite ends, closing both access apertures of said container with end closure means to exclude air and moisture therefrom and to thereby store said lyophilized material in an aliquot amount, opening both access apertures of said container, interposing said container between a needle and a barrel of a hypodermic syringe with one access aperture of said container in communication with said needle and the other access aperture of said container in communication with said barrel, and drawing a reconstituting liquid into said hypodermic barrel through said hypodermic needle and through said container to reconstitute said lyophilized material and to form an administerable dose of a tracing substance for use with a radionuclide dose.

* * * * *